(12) United States Patent
Bjernulf et al.

(10) Patent No.: US 10,047,869 B2
(45) Date of Patent: *Aug. 14, 2018

(54) VERSATILE ROTARY VALVE

(71) Applicant: GE Healthcare Bio-Sciences AB, Uppsala (SE)

(72) Inventors: Olle Bjernulf, Uppsala (SE); Christer Olof Eriksson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/486,272

(22) Filed: Apr. 12, 2017

(65) Prior Publication Data

US 2017/0248240 A1 Aug. 31, 2017

Related U.S. Application Data

(63) Continuation of application No. 14/422,463, filed as application No. PCT/SE2013/050985 on Aug. 21, 2013, now Pat. No. 9,625,044.

(30) Foreign Application Priority Data

Aug. 22, 2012 (SE) ...................................... 1250942

(51) Int. Cl.
*F16K 11/076* (2006.01)
*G01N 30/38* (2006.01)

(52) U.S. Cl.
CPC ............ *F16K 11/076* (2013.01); *G01N 30/38* (2013.01); *Y10T 137/86654* (2015.04)

(58) Field of Classification Search
CPC .............................. F16K 11/076; G01N 30/38
See application file for complete search history.

(56) References Cited

U.S. PATENT DOCUMENTS 2,745,434 A 5/1956 Stevenson
3,757,492 A 9/1973 Graff
(Continued)

FOREIGN PATENT DOCUMENTS

CN 101432557 A 5/2009
CN 101730844 A 6/2010
(Continued)

OTHER PUBLICATIONS

Supplemental European Search Report received for European Patent Application No. 13830660.0, dated Mar. 16, 2016, 11 pages.
(Continued)

*Primary Examiner* — Craig Schneider
*Assistant Examiner* — Kevin Barss
(74) *Attorney, Agent, or Firm* — Wood IP LLC

(57) ABSTRACT

A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more interconnection paths for selective fluidic interconnection of said valve orifices with respect to the rotor position, wherein the stator comprises, an inlet port, an outlet port, a component feed port, a component return port, and wherein the interconnection paths in the rotor are arranged to: —in a first rotor position interconnect the inlet port with the outlet port, —in a second rotor position interconnect the inlet port with the component feed port and the component return port with the outlet port, —in a third rotor position interconnect the inlet port with the component return port and the component feed port with the outlet port.

11 Claims, 15 Drawing Sheets

(56) References Cited

U.S. PATENT DOCUMENTS

| | | | |
|---|---|---|---|
| 4,182,184 | A | 1/1980 | Bakalyar et al. |
| 4,469,494 | A | 9/1984 | Weenen |
| 4,968,334 | A | 11/1990 | Hilton |
| 5,176,722 | A | 1/1993 | Lemcoff et al. |
| 5,268,021 | A | 12/1993 | Hill et al. |
| 5,681,376 | A | 10/1997 | Wooten et al. |
| 8,257,586 | B2 | 9/2012 | Dehmer |
| 9,625,044 | B2 * | 4/2017 | Bjernulf ............... F16K 11/076 |
| 2001/0035516 | A1 | 11/2001 | Nichols et al. |
| 2003/0098076 | A1 | 5/2003 | Nichols |
| 2005/0061722 | A1 | 3/2005 | Takao et al. |
| 2009/0071341 | A1 | 3/2009 | Takemasa et al. |
| 2010/0058841 | A1 | 3/2010 | Wilen |
| 2011/0240899 | A1 | 10/2011 | Wilen |
| 2012/0103887 | A1 | 5/2012 | Maeda et al. |
| 2012/0145937 | A1 | 6/2012 | Richman et al. |

FOREIGN PATENT DOCUMENTS

| | | | |
|---|---|---|---|
| CN | 102209863 | A | 10/2011 |
| DE | 4425393 | A1 | 1/1996 |
| EP | 0512534 | A1 | 11/1992 |
| EP | 0853967 | A2 | 7/1998 |
| EP | 0853967 | A3 | 11/1998 |
| EP | 2888595 | A1 | 7/2015 |
| WO | 2008/140374 | A1 | 11/2008 |
| WO | 2010/056189 | A1 | 5/2010 |
| WO | 2010/139359 | A1 | 12/2010 |
| WO | 2012/074481 | A1 | 6/2012 |
| WO | 2014/031069 | A1 | 2/2014 |

OTHER PUBLICATIONS

International Preliminary Report on Patentability received for PCT Patent Application No. PCT/SE2013/050985, dated Feb. 24, 2015, 5 pages.
International Search Report and Written Opinion received for PCT Patent Application No. PCT/SE2013/050985, dated Nov. 25, 2013, 9 pages.
Non-Final Office Action received for U.S. Appl. No. 14/422,463, dated Apr. 1, 2016, 10 pages.
Final Office Action received for U.S. Appl. No. 14/422,463, dated Sep. 27, 2016,10 pages.
Notice of Allowance received for U.S. Appl. No. 14/422,463, dated Dec. 15, 2014, 8 pages.
Office Action Received for Chinese Patent Application No. CN201380043520, dated Jan. 27, 2016.

* cited by examiner

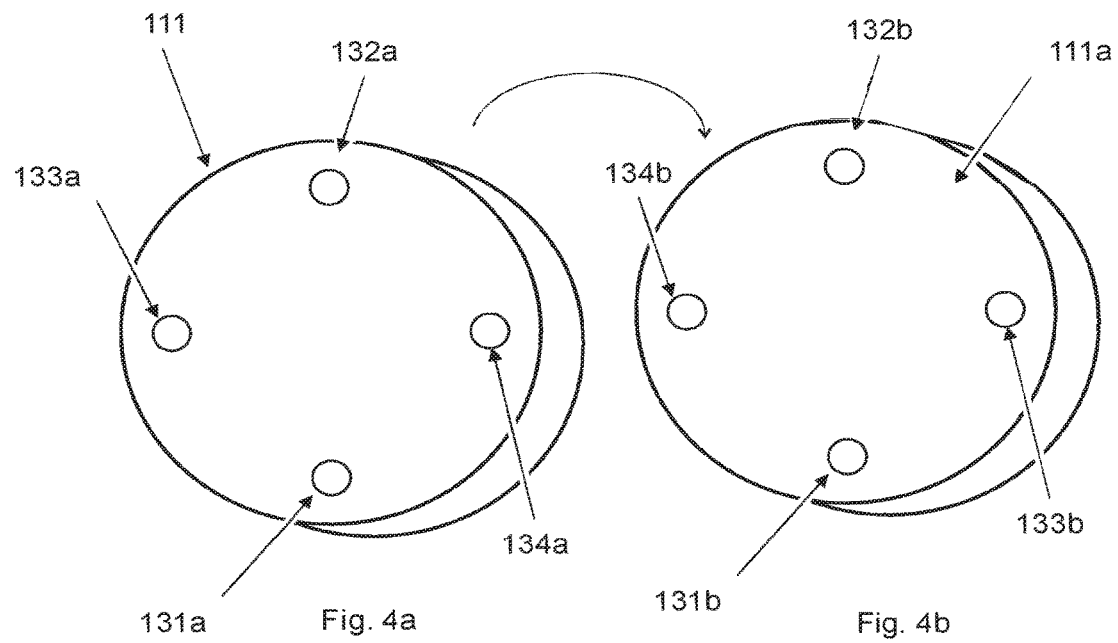
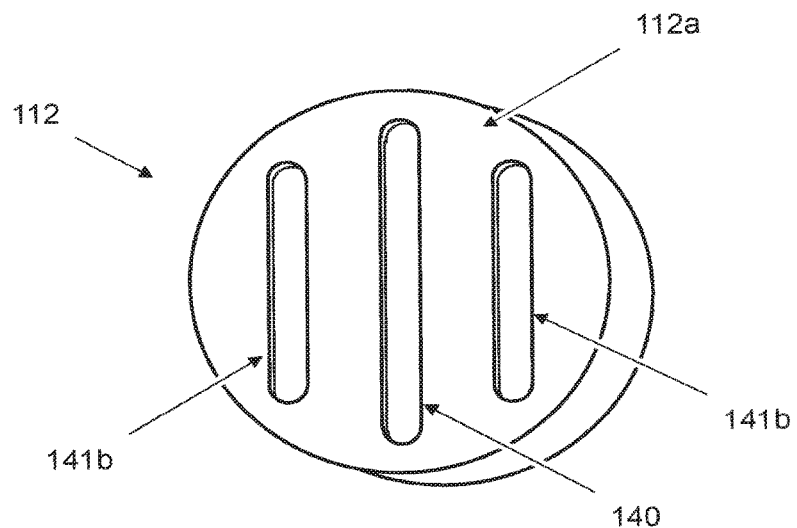

VERSATILE ROTARY VALVE

FIELD OF THE INVENTION

The present invention relates to valves and more specifically to rotary valves for selectively enabling components into a main flow.

BACKGROUND

Valves are commonly used in devices that involve the transportation of a fluid. A typical type of valve, for example used in laboratory systems of moderate sizes, is the rotary valve.

Generally, a rotary valve has a stationary body, herein called a stator, which co-operates with a rotating body, herein called a rotor.

The stator is provided with a number of inlet and outlet ports. The ports are via bores in fluid communication with a corresponding set of orifices on an inner stator face. The inner stator face is an inner surface of the stator that is in fluid tight contact with an inner rotor face of the rotor. The rotor is typically formed as a disc and the inner rotor face is pressed against the inner stator face in rotating co-operation. The inner rotor face is provided with one or more grooves which interconnect different orifices depending on the rotary position of the rotator with respect to the stator.

Rotary valves can be designed to withstand high pressures (such as pressures above 25 MPa). They can be made from a range of materials, such as stainless steel, high performance polymeric materials and ceramics.

The number of inlets/outlets as well as the design of grooves in the rotor or the stator reflects the intended use of a specific valve.

A common type of multi-purpose valve has one inlet port (typically placed in the rotary axis of the valve) and a number of outlets ports that are placed equidistantly around the inlet port. The rotor has a single, radially extending groove that has one end in the rotary centre, thereby always connecting to the inlet, while the other end connects to any one of the outlets depending on the angular position of the rotor with respect to the stator. Such a valve is useful to direct a flow from the inlet to any of the outlets—one at a time.

More complicated arrangements, tailor-made to perform one or several specific tasks, are possible. For instance, rotary valves may be used to introduce a component into the fluid path of an analytical system.

In many instruments handling a flow of a liquid, such as liquid chromatography systems (LCS), there is sometimes a need to be able to either include or to bypass a component.

This situation is easily solved with a conventional 4-way double-path valve, schematically shown in FIGS. 1 and 2.

However, it would be beneficial to be able to integrate more functionalities such as the ability to reverse the flow through the component into a single valve. One reason for this would be to save cost (e.g. since there is need for one valve motor drive only in the case of an automatically operated valve). Another reason would be the possibility to shorten path lengths by integrating as much paths into the valve as possible, thereby reducing the need for interconnecting tubing.

Thus, there is a need for a multipurpose valve that can be used for many situations where components need to be connected to/disconnected from a main flow.

SUMMARY OF THE INVENTION

The object of the invention is to provide a rotary valve, which valve overcomes one or more drawbacks of the prior art. This is achieved by the rotary valve as defined in the independent claim. There is further provided a chromatography system comprising at least one such rotary valve.

Hereby one single rotary valve is achieved which can take at least three different rotary positions, in which a component may be connected in forward and reverse flow or be bypassed. This will both give a cheaper valve compared to using two separate valves and minimize interconnecting tubings.

According to one aspect, there is provided A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more interconnection paths for selective fluidic interconnection of said valve orifices with respect to the rotor position, wherein the stator comprises, an inlet port, an outlet port, a component feed port, a component return port, and wherein the interconnection paths in the rotor are arranged to:
  in a first rotor position interconnect the inlet port with the outlet port,
  in a second rotor position interconnect the inlet port with the component feed port and the component return port with the outlet port,
  in a third rotor position interconnect the inlet port with the component return port and the component feed port with the outlet port.

According to a second aspect, there is provided a rotary valve wherein
the interconnection paths in the rotor are arranged to:
  in a fourth rotor position interconnect the component feed with the component return port.

A more complete understanding of the present invention, as well as further features and advantages thereof, will be obtained by reference to the following detailed description and drawings.

BRIEF DESCRIPTION OF THE DRAWINGS

FIG. 4a is a perspective view of the front side of a stator according to a first embodiment of the invention.

FIG. 4b is a perspective view of the stator of FIG. 4a viewed from the other side, i.e. from the inner stator face side.

FIG. 5 is a perspective view of a rotor of the first embodiment of the invention from the rotor inner face.

FIG. 9b schematically shows the elution phase of the purification process of FIG. 9a.

FIG. 9c schematically shows the second step of the purification process of FIG. 9a.

FIG. 12b schematically shows a second step in the process of FIG. 12a.

DETAILED DESCRIPTION OF EMBODIMENTS OF THE INVENTION

Figure 1:
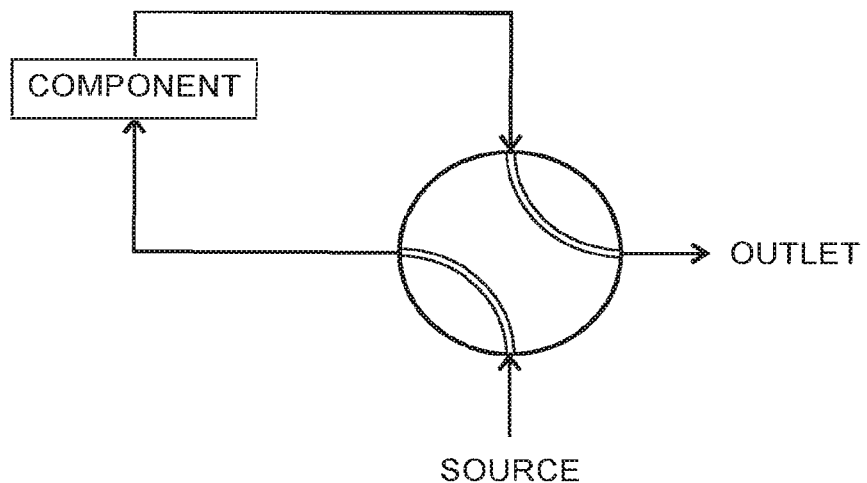
FIG. 1 shows flow through a component using a conventional valve in a first mode.
Figure 2:
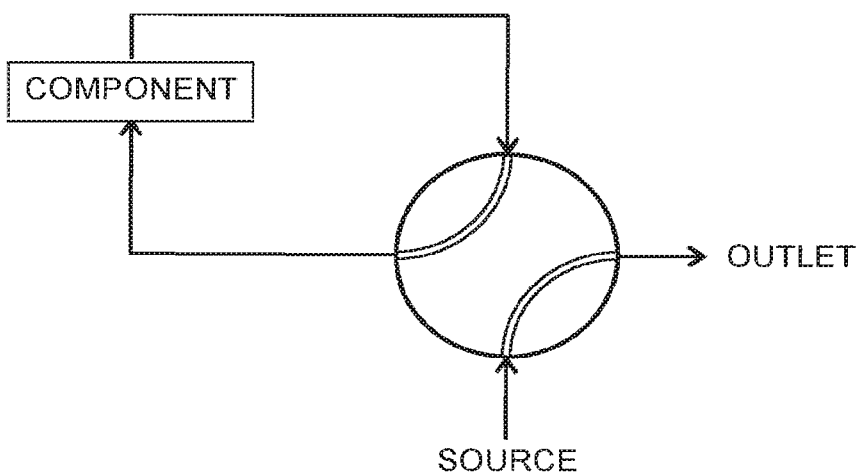
FIG. 2 shows bypassing the component of FIG. 1 using a conventional valve in a second mode.
Figure 3:
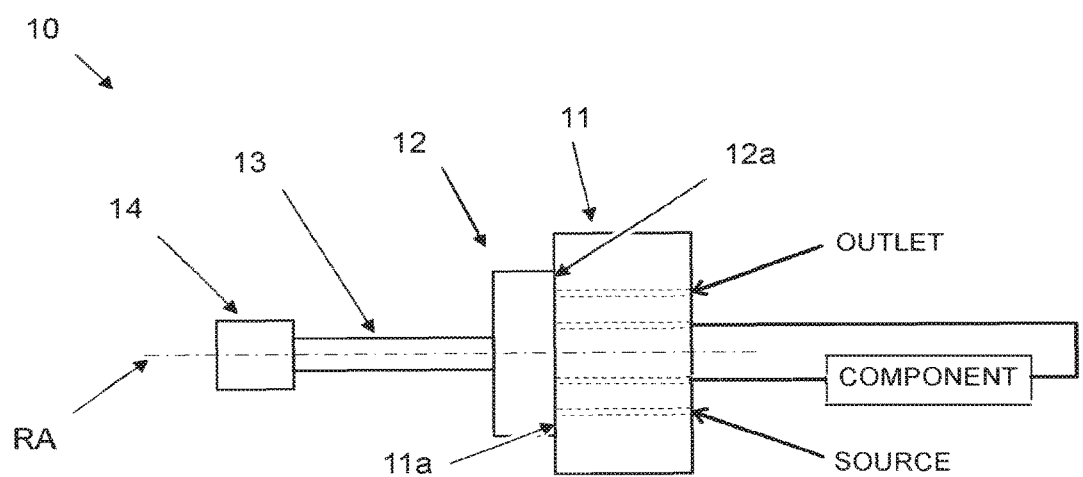
FIG. 3 is a schematic side view of a rotary valve according to one embodiment of the present invention.

The main parts of a typical rotary valve are schematically shown in FIG. 3 (wherein no brackets or similar load carrying or fastening elements are shown). The rotary valve 10 has a stator 11, a rotor 12, a rotary shaft 13 that optionally may be provided with means (not shown) for recognizing its angular position and a driving unit 14 typically comprising a gear box and a motor (although a valve also may be operated manually). The rotor is rotatable with respect to the stator around a rotary axis RA of the valve.

The stator 11, which is fixed with respect to the instrument into which it is built, is provided with ports indicated by dotted lines for fluid communication with a fluid source/outlet and any component with which the valve is to co-operate. The ports may be positioned on any suitable part of the stator, and in any suitable direction. The ports are provided with means to connect capillaries or tubing. Such means may be of any suitable type, such as conventional Valco fittings well known to anyone skilled in the art. The ports are via channels in fluid communication with a corresponding set of valve orifices on an inner stator face 11a, i.e. the surface of the stator that during operation is in contact with the rotor 12.

The rotor 12 is typically formed as a disc and has an inner rotor face 12a that is pressed against the flat inner stator face 11a during operation to achieve sealing contact there between. The inner rotor face 12a is provided with one or more interconnection paths which interconnect different valve orifices of the inner stator face 11a depending on the rotary position of the rotor with respect to the stator. The interconnection paths may be any type of path capable of providing fluidic contact between two valve orifices, and may be comprised of an internal channel with discrete orifices, grooves in the inner rotor face or the like.

FIG. 4a, which shows a simplified perspective view of the front side of a stator 111, illustrates the inlet and outlet port arrangement for one embodiment of a valve according to the present invention.

Generally, it should be noticed that the angular position of ports, grooves and similar shown in the figures of the present application could differ between different embodiments of the invention, i.e. they could be turned with respect to the rotary axis of the valve, mirrored or altered in other ways as long as their mutual co-operation is still according to the inventive idea.

In addition, since the inlet/outlet ports are connected to orifices on the inner stator face 11a via bores (or any type of channels) it is possible to arrange the ports in a way that differs from the pattern on the inner stator face 11a by making non-linear channels between the ports and the orifices. However, for reasons of simplicity, the ports are shown as being positioned in-line with the inner stator face orifices.

Thus, the stator 111 of the disclosed embodiment has four ports 131a-134a that are used to connect the valve to all desired operative components of the instrument.

An inlet port 131a is a port used as inlet port from a first liquid source of the instrument such as a pump, typically via a set of components of the instrument such as detectors, other valves etc., and any connected components such as a chromatography column. An outlet port 132a serves as an outlet port from which the liquid is allowed to exit to the remaining part of the instrument or out from the instrument.

A component, such as a chromatography column, a conductivity monitor or a flow restrictor device or the like, is connectable to the valve via a component feed port 133a and a component return port 134a, whereby the feed port 133a acts as an outlet from the valve and the return port 134a as an inlet to the valve for the returning flow from the first component, or the opposite way around in case the flow is reversed as will be disclosed in more detail below.

FIG. 4b is a perspective view of the stator 111 of FIG. 4a viewed from the other side, i.e. the inner stator face side 111a. Note that each port is connected to the inner stator face 111a via a channel ending in a corresponding orifice, an inlet valve orifice 131b, an outlet valve orifice 132b, a component feed valve orifice 133b, a component return valve orifice 134b shown in FIG. 4b.

The positions for valve orifices are equally distributed around the center of the stator (which center coincides with the rotary axis of the valve). As described above the positions of the orifices and the partition angle there between can be varied without departing from the inventive idea. Since there are four such positions on the stator according to the embodiment, the partition angle is 90°. All positions are placed with essentially the same radial distance to the rotational axis of the valve.

One embodiment of an inner rotor face 112a of a rotor 112 for cooperation with the stator 111 above is shown in FIG. 5. It is provided with three interconnection paths for selective fluidic interconnection of the valve orifices in the inner stator face 111a with respect to the rotor position in the form of grooves in the inner rotor face 112a. A diagonal groove 140 is arranged to provide an interconnection path between diagonally arranged the valve orifices 131b and 132b, and 133b and 134b respectively. Two parallel grooves 141 are arranged to provide interconnection paths 141a and 141b between two adjacent valve orifices in order to connect a component into the flow path when the rotor is positioned at 45° with respect to the position of the diagonal groove 140.

When assembled, the inner rotor face 112a is pressed against the inner stator face 111a in a manner that is typical for any conventional rotary valve (which is well known for anyone skilled in the art, and will not be explained herein). Depending on the mutual angular positions of the rotor 112 and the stator 111 different operation modes are obtained for the valve. These are illustrated in FIGS. 6a to 6d, wherein the interconnection grooves of the rotor are schematically indicated by thick broken lines, and the fluid flow in the valve by an arrow.

Figure 6A:
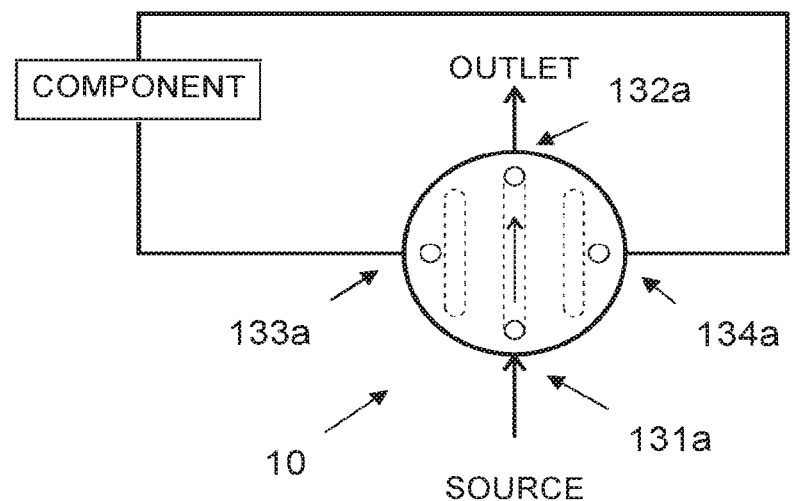
FIG. 6a is a schematic view of an embodiment of the rotary valve with the rotor positioned at a first rotor position.

In the first rotor position, as shown in FIG. 6a, the valve 10 is arranged to bypass the component ports 133a and 134a. The fluid flow enters the inlet port 131a, goes via the first orifice 131b through the diagonal rotor groove 140 and exits the valve through the outlet port 132a (via the second orifice 132b). The other ports and grooves of the valve are not active in the first rotor position, i.e. the component is bypassed.

Figure 6B:
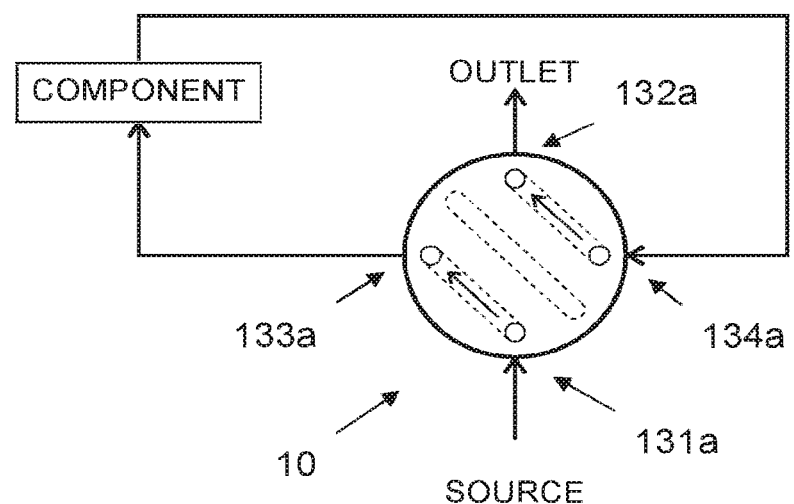
FIG. 6b is the rotary valve of FIG. 6a at a second rotor position.

FIG. 6b shows the valve 10 in a second rotor position wherein the interconnection paths in the rotor 12 interconnect the inlet port 131a with the component feed port 133a and the component return port 134a with the outlet port 132a. In this rotor position, the component is connected into the fluid flow in a forward flow connection. More specifically, the parallel groove 141a interconnects the valve orifice 131b of the inlet port and the valve orifice 133b of the component feed port 133a, while the other parallel groove 141b interconnects the valve orifice 134b of the component return port 134a and the valve orifice 132b of the outlet port 132a.

Figure 6C:
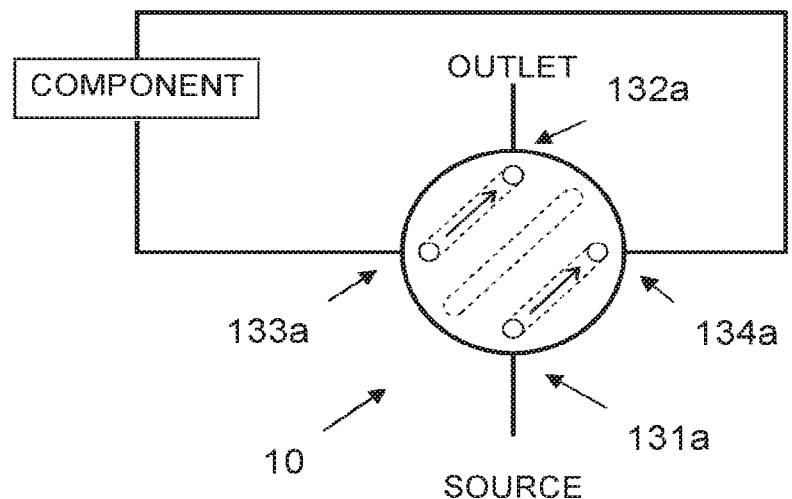
FIG. 6c is the rotary valve of FIG. 6a at a third rotor position.

FIG. 6c shows the valve 10 in a third rotor position wherein the interconnection paths in the rotor 12 interconnect the inlet port 131a with the component return port 134a and the component feed port 133a with the outlet port 132a. In this rotor position, the component is connected into the fluid flow in a reversed flow connection. More specifically, the parallel groove 141a interconnects the valve orifice 131b of the inlet port and the valve orifice 134b of the component return port 134a, while the other parallel groove 141b interconnects the valve orifice 133b of the component feed port 133a and the valve orifice 132b of the outlet port 132a.

Figure 6D:
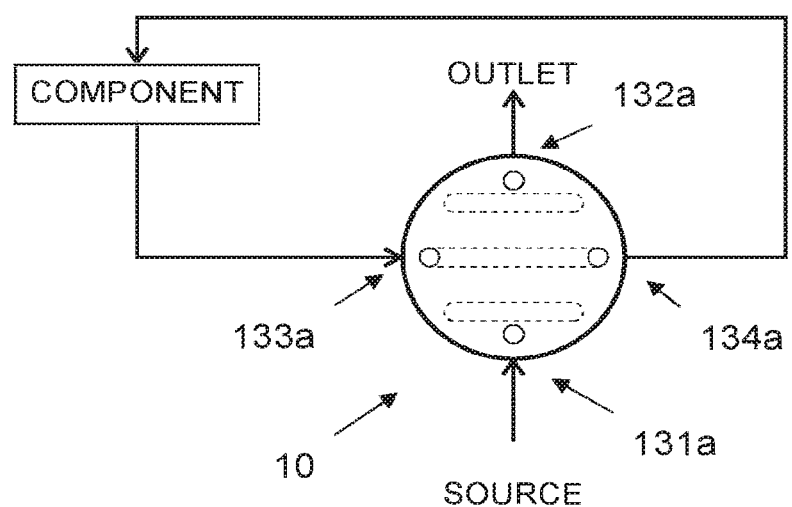
FIG. 6d is the rotary valve of FIG. 6a at a fourth rotor position.

FIG. 6d shows the valve 10 in a fourth rotor position wherein the interconnection paths in the rotor 12 interconnect the component feed port 133a with the component return port 134a whereby the flow path between the main inlet port 131a and the outlet port 132a.

As described above the exact position of the orifices need not to be according to the embodiment described above. What is important for the invention is that the different grooves reaches the specific orifices that should be reached in each rotation position described above. Throughout the disclosure, the terms input and output have been used to indicate the function of specific ports with respect to the disclosed embodiment where the valve is arranged to select input fluids to two pumps of a chromatography system. The valve according to the present invention may be used in other applications wherein the versatile functionality may be beneficial and where one or more of the input ports may instead serve as output ports and the other way around.

The present invention is described with respect to a component selection valve, but it should be noted that the configuration of the valve makes it very versatile, and it can be used in a large range of applications in analytical instruments or process systems, especially in chromatography systems.

Figure 7A:
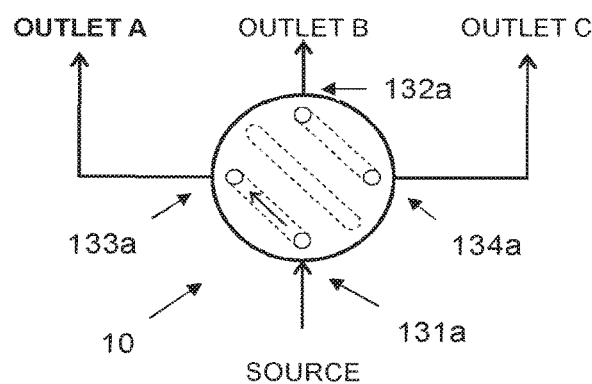
FIG. 7a is a schematic view of an alternative employment of the rotary valve at a first rotor position.
Figure 7B:
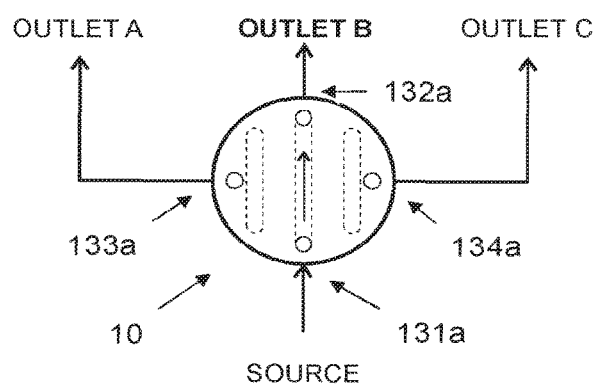
FIG. 7b is a schematic view of the rotary valve of FIG. 7a at a second rotor position.
Figure 7C:
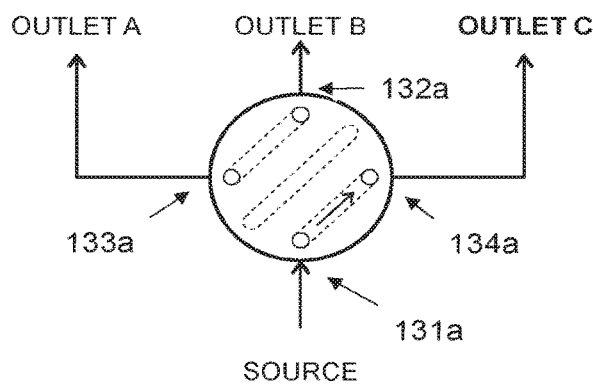
FIG. 7c is a schematic view of the rotary valve of FIG. 7a at a third rotor position.

FIGS. 7a-7c schematically shows one embodiment, wherein the present rotary valve 10 is connected as an output selection valve capable of directing the flow from a source inlet 131a to either one of three outlets A-C, 132a-134a. However it should be noted that the flow may alternatively be in the opposite direction and the rotary valve being arranged to select one of three input sources.

Figure 8:
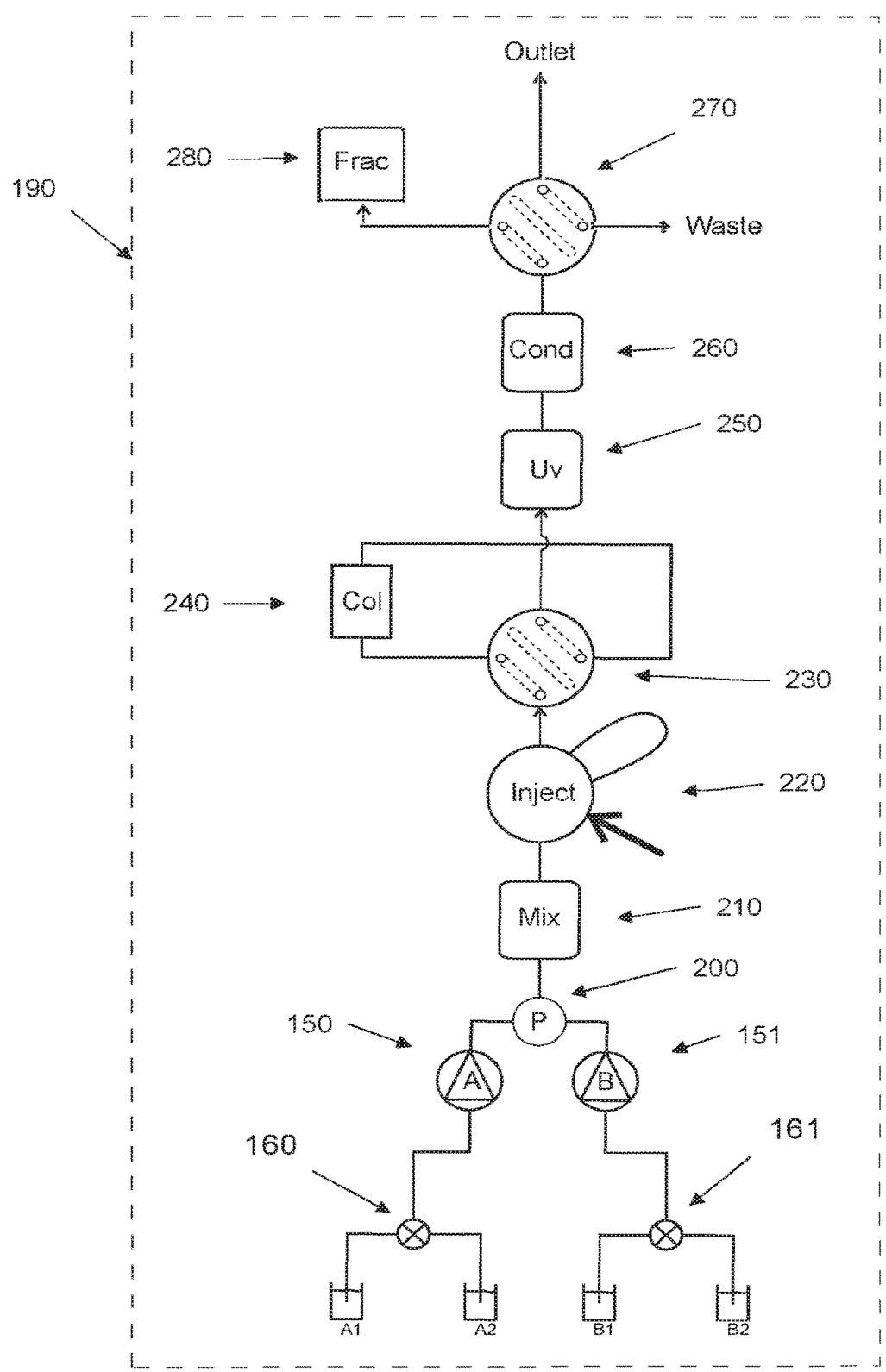
FIG. 8 schematically shows one embodiment of a chromatography system comprising the rotary valve.

FIG. 8 schematically shows one embodiment of a chromatography system 190 comprising two input 3-way valves 160 and 161, arranged to select the input fluid from fluid sources A1, A2, B1, B2 for two system pumps 150 and 151. Said chromatography system 190 may further comprise:
 a pressure sensor 200 for registering the system pressure in the flow path after the system pumps,
 a mixer 210 to ensure appropriate mixing of the fluids supplied by the pumps,
 an injection valve 220 for injecting a sample into the fluid path,
 a column connection valve 230 for selectively connecting/disconnecting a column 240 in the fluid path.
 an ultraviolet (UV) monitor 250 for detecting the output from the column.
 a conductivity monitor 260, and
 an output selection valve 270 with two or more output positions, e.g. connected to a fraction collector 280, a waste receptacle or the like.

FIG. 8 shows one embodiment of a chromatography system wherein the present valve 10 is used in two different positions, i.e. as column connection valve 230 as is disclosed in FIGS. 6a-6d and as output selection valve 270 as is disclosed in FIGS. 7a-7c.

The chromatography system of FIG. 8 represents an example of how a chromatography system may be constructed, and other embodiments may be of different design comprising two or more of some components and potentially lack some of said components. According to one embodiment, the chromatography system is a liquid chromatography system.

Figure 9A:
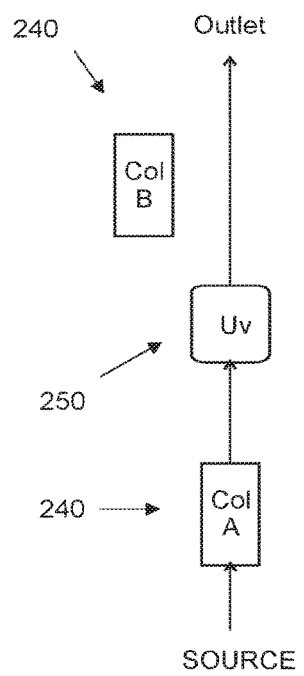
FIG. 9a schematically shows the first step of a two-step purification process.
Figure 9B:
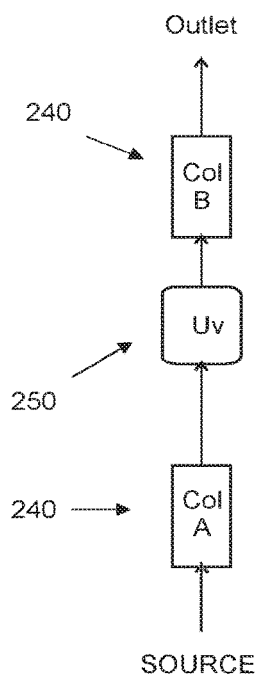
Figure 9C:
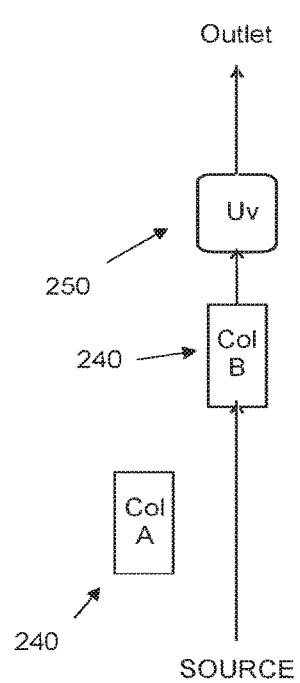

The versatile nature of the present rotary valve 10 may further be illustrated by some application specific examples where the valve provides substantial benefits in flow path design and over all operation. FIGS. 9a-9c schematically show a two-step purification process which may be simplified by an arrangement using rotary valve 10 of the present design. In a two-step purification process of this type, the first step shown in FIG. 9a typically involves capture of a target sample such as a protein in a first column A 240, e.g. an affinity column or the like. In order to monitor the capture of the target sample, an UV monitor 250 is connected in the flow path following column A. The capture phase process may conventionally comprise a wash phase wherein non target molecules or the like are washed out from column A, also the wash phase is monitored by the UV monitor to determine when all non-targets have been washed out. During the capture/wash phase, the second column B is not connected as indicated in FIG. 9a. When the output signal from the UV monitor indicates that the capture/wash phase is completed, the next phase is to elute the target sample from column A and further purify it using column B. In order to elute the target sample from col A an elution buffer or the like is supplied to the source whereby the target sample is released from the column A. During the elution phase the output from column A is monitored using the UV monitor to identify when the target sample reaches the UV monitor whereby column B is connected in the fluid path following the UV monitor to receive the target sample, as is shown in FIG. 9b, and then to discontinue the elution process when all target sample is loaded on column B and initiate the third phase which is the second purification step. In the second purification step, as is shown in FIG. 9c, column A is preferably disconnect from the flow path, and the elution buffer is normally replaced with a second purification buffer to drive the chromatographic purification in column B. In this step it is desirable to monitor the output from column B by introducing the UV monitor at the output end of column B. Thus, in the third phase, the logical order of column B and the UV monitor need to be altered compared to the previous step. Unless there are two separate UV monitors available, the process of altering the logical order of two fluidic components is a non trivial operation which requires several valve components. Further, in some situations it is desirable to introduce the eluted target sample from column A onto column B as quickly as possible and then change buffer as quick as possible, e.g. as the buffer used during elution may make the protein unstable.

FIGS. 10a to 10d shows an example of how a two-step purification process may be designed using an arrangement comprising three rotary valves 10a-10c of the present design. In this arrangement, three rotary valves 10a-10c are connected in series source to outlet. A column A 240 is connected between the two component feed and return ports of valve 10a as disclosed in FIGS. 6a to 6d enabling column A to be connected and disconnected from the flow path. A second column B 240 is connected between the component feed ports of the second and third valves 10b and 10c, respectively, and an UV monitor 250 is connected between the component return ports of the second and third valves 10b and 10c, respectively. By this arrangement efficient alternation of the logical order of column B and the UV monitor is enabled using only two valves, while also allowing bypass of both components as well as individual connection of the components to the flow path.

Figure 10A:
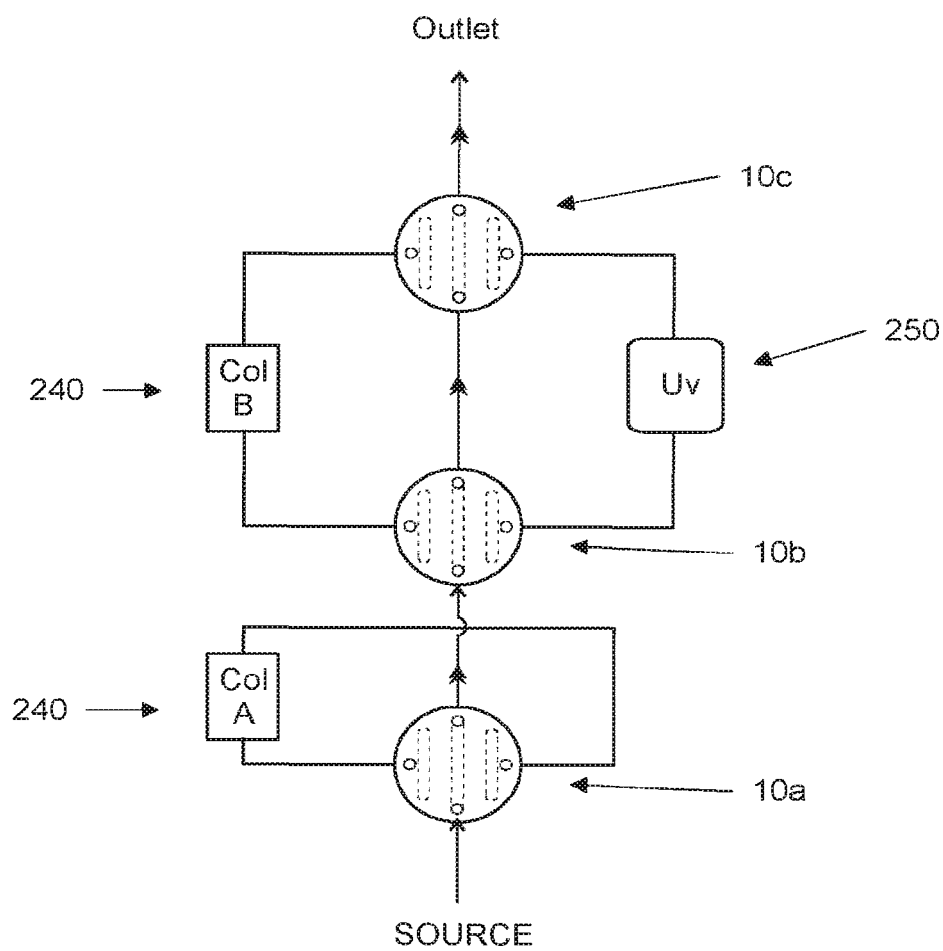
FIG. 10a schematically shows a fluidic circuit in a bypass mode for performing the two-step purification process of FIGS. 9a-9c.
Figure 10B:
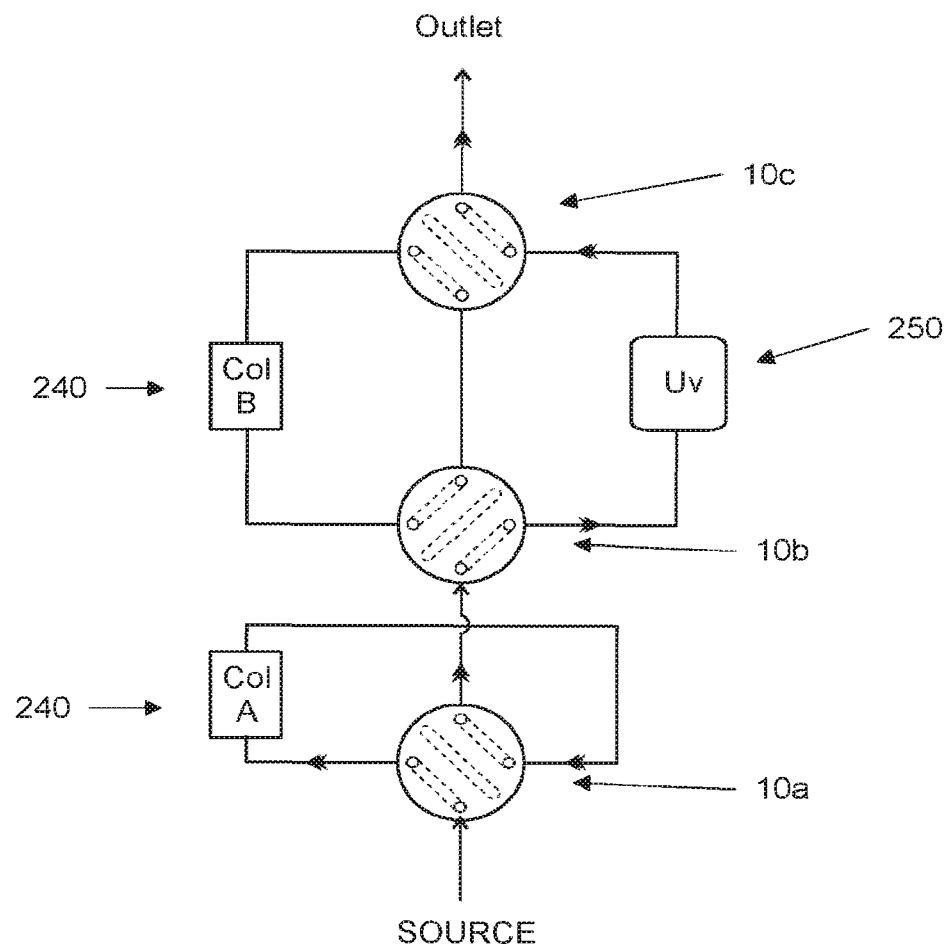
FIG. 10b schematically shows a fluidic circuit in a capture/wash phase and a initial elution phase for performing the two-step purification process of FIGS. 9a-9c.
Figure 10C:
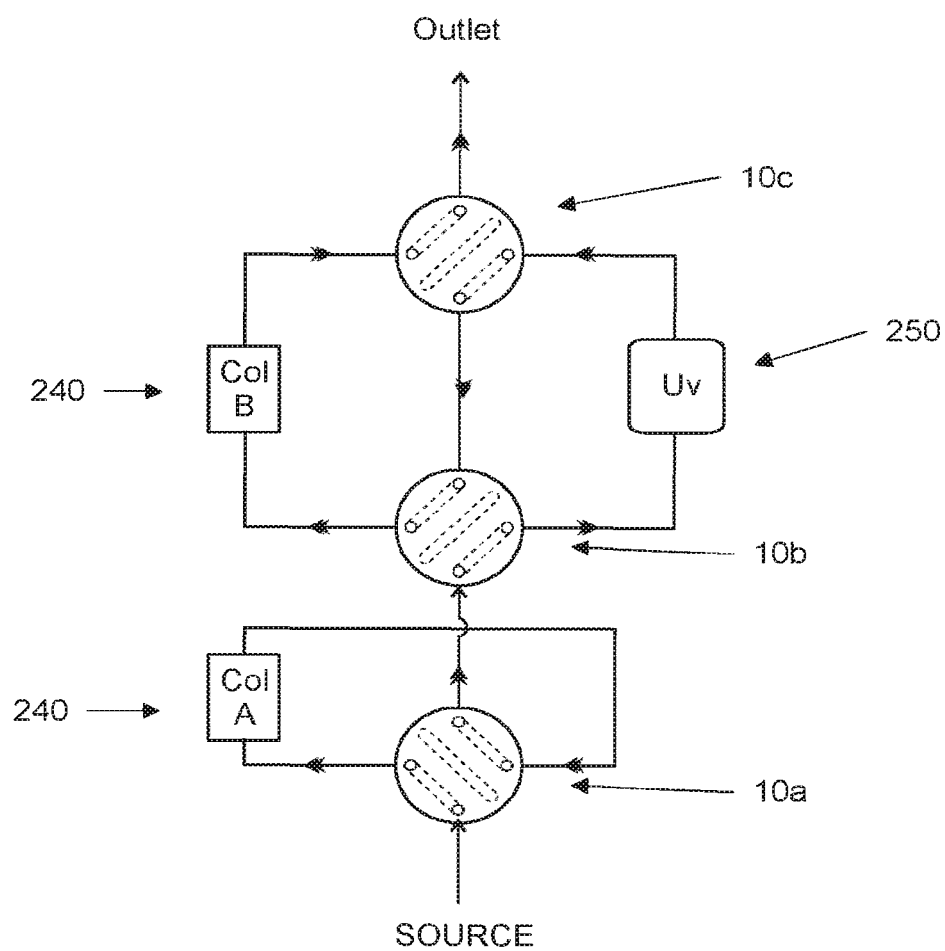
FIG. 10c schematically shows a fluidic circuit in an elution phase for performing the two-step purification process of FIGS. 9a-9c.
Figure 10D:
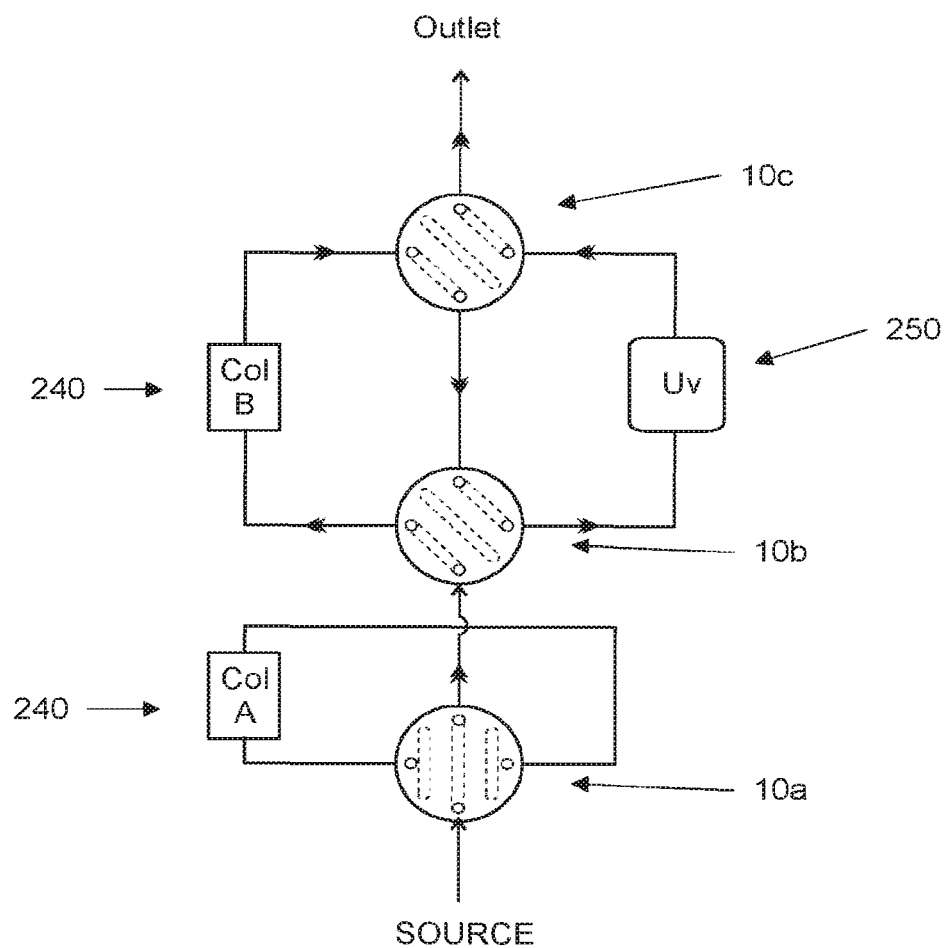
FIG. 10d schematically shows a fluidic circuit in a phase that represents the second purification step of the two-step purification process of FIGS. 9a-9c.

In FIG. 10a all three valves 10a-10c are arranged in bypass mode, first position, whereby the fluid flow goes straight through from the source to the outlet. FIG. 10b represents the capture/wash phase and the initial elution phase wherein the fluid flow is directed through column A and the UV monitor, whereas column B remains disconnected. This is achieved by setting valve 10a in second position, valve 10b in third position and valve 10c in second position. FIG. 10c represents the elution phase where the target sample has been detected by the UV monitor and the second column B has been connected after the UV monitor. This is achieved by keeping valve 10a in second position, keeping valve 10b in third position and setting valve 10c in third position. Note that connection of column B after the UV monitor by switching position of valve 10c from second to third position only. FIG. 10d represents the second purification step where column A is disconnect from the flow path, and the logical order of column B and the UV monitor has been altered. This is achieved by setting valve 10a in first position, valve 10b in second position and valve 10c in second position.

The above embodiment represents one example of use when altering the logical order of components in the flow path is beneficial, this arrangement may further be used in any application wherein this functionality is useful. By altering the logical order of components in the flow path using two valves 10b and 10c connected to two components in accordance with FIGS. 10a to 10d one can create different flow path configurations that optimize the use of available components in each step. E.g. the position of UV monitor, outlet valve or columns can be altered to best suit current application. As is clear from above, such an arrangement for altering the logical order of components in the flow path can generally be achieved by a fluidic circuit comprising a first and a second rotary valves 10a and 10b and a first and a second fluidic component, wherein the inlet port of the second valve is connected to the outlet port of the first valve, the first fluidic component is connected between the component feed port of the first valve and the component feed port of the second valve, and the second fluidic component is connected between the component return port of the first valve and the component return port of the second valve.

Figure 11A:
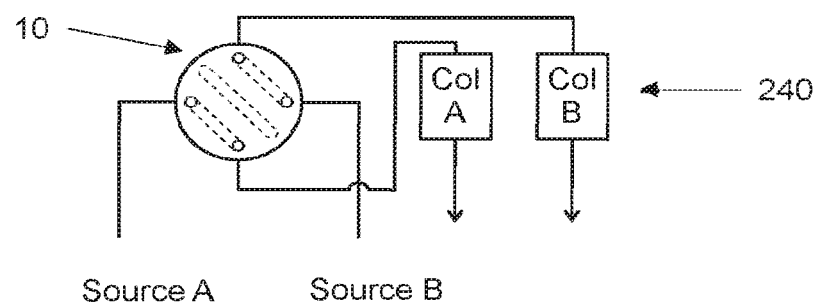
FIG. 11a is a schematic view of an alternative employment of the rotary valve 10 in a first position.
Figure 11B:
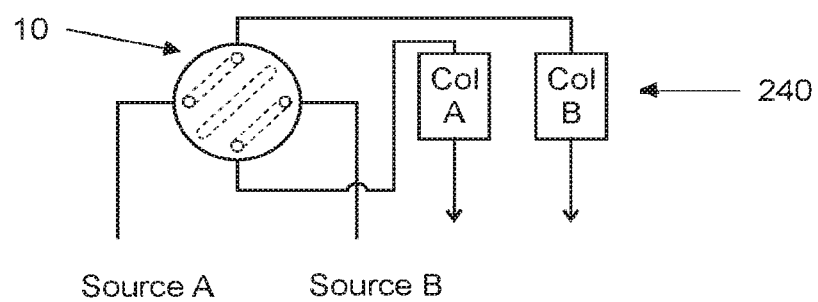
FIG. 11b is a schematic view of an alternative employment of the rotary valve 10 of FIG. 11a in a second position.

Further, the present valve 10 may be used as a switch between two independent fluid paths as is indicated in FIGS. 11a and 11b, wherein a source A and B are connected to the component ports, respectively and column A and B are connected to the inlet and outlet respectively. In this configuration the valve enables selective connection of source A or B to the respective columns A and B. One application where such an arrangement would be useful is to perform conditioning of one column in parallel with running a chromatographic process in the other column, e.g. in a bioprocess production flow path, wherein the conditioned column may be switched into the chromatography process and the other column disconnected for cleaning or replacement.

Figure 12A:
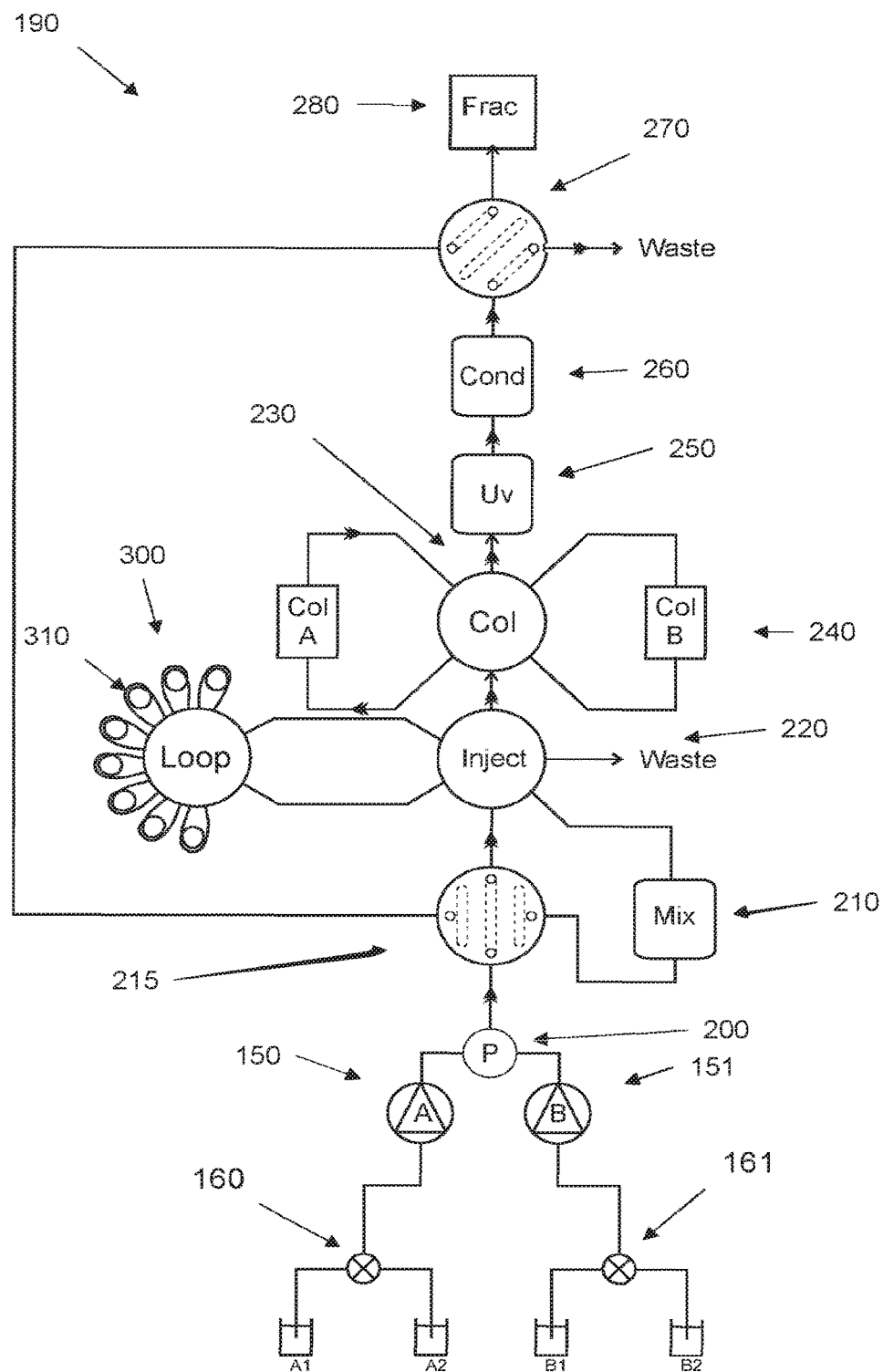
FIG. 12a schematically shows a first step in a purification process where an alternative employment of the rotary valve 10 is used in a chromatography system.
Figure 12B:
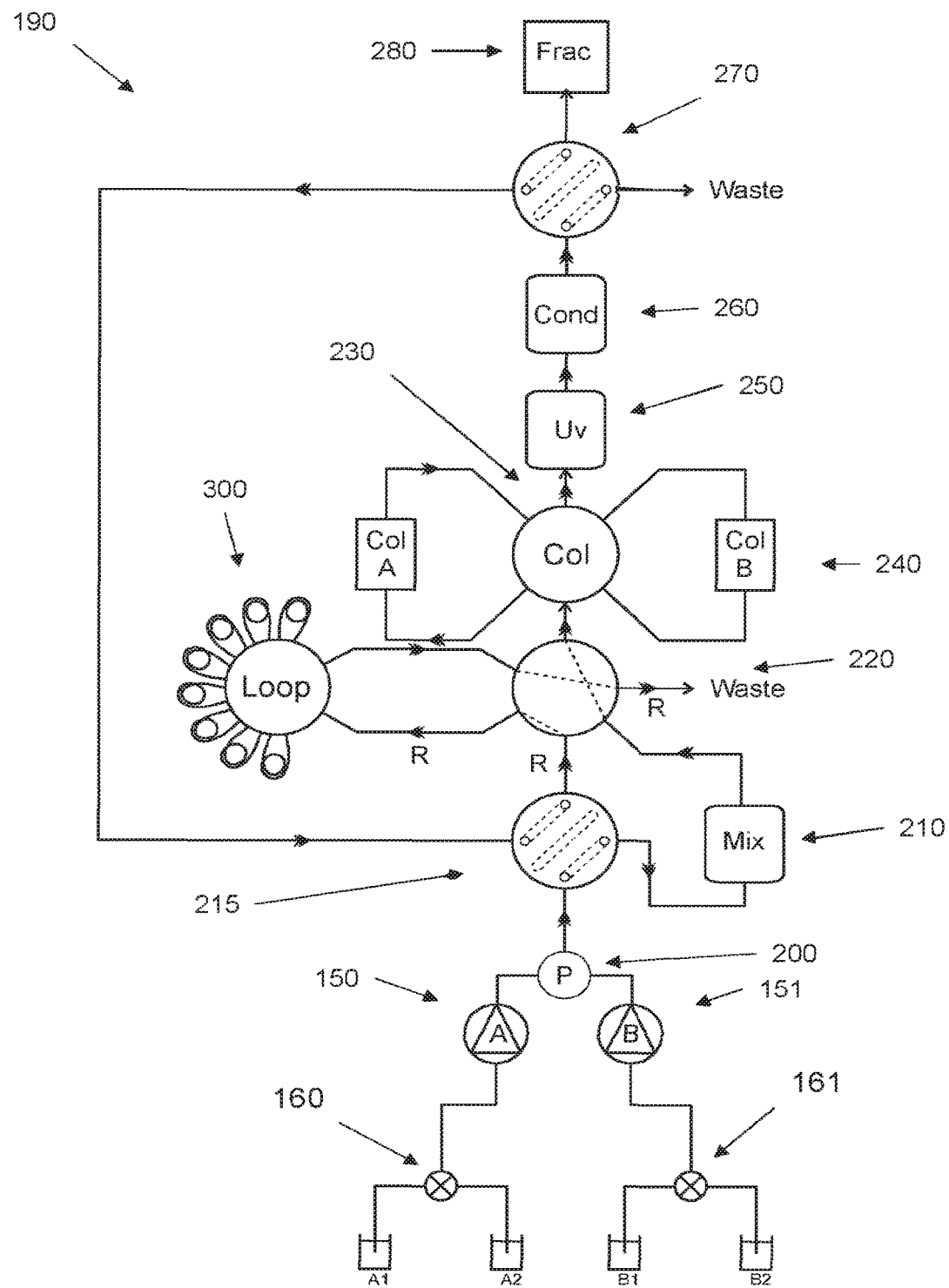

FIGS. 12a-12 schematically show another application specific example where the present valve 10 is introduced in an alternative position in the flow path of the chromatography system 190 of FIG. 8 in order to enable an alternative two-step purification process wherein eluted sample fractions are stored in sample loops for performing a subsequent second purification step. In the system 190 of FIGS. 12a and 12b a valve 215 has been introduced in the flow path before the injection valve 220 with the outlet port connected to an inlet port of the injection valve 220. The mixer 210 is connected between one of the component ports of valve 215 and a second inlet port on the injection valve 220. The other component port of the valve 215 is connected to an outlet ports of output selection valve 270. Further, in FIGS. 12a and 12b a loop valve 300 is connected to respective outlet and inlet of the injection valve. In the disclosed embodiment, 8 sample loops 310 are shown connected to the loop valve 300 each capable of collecting a sample volume for subsequent purification in accordance with common practice in the field. In an alternative embodiment, the loop functionality may be integrated in the injection valve 220. Compared with FIG. 8, the column selection valve 230 is replaced by a valve capable of connecting two or more columns to the fluid path, illustrated by column A and B 240.

FIG. 12 schematically show the first purification step wherein the target sample is introduced in the fluid path and captured and washed in column A, the liquid flow is indicated by arrows. Like in the above example illustrated in FIGS. 9 and 10, the same setup is initially used for initial elution, optionally with the mixer connected in the flow path. When the first target sample is detected by the UV-monitor 250, valves 215 and 270 are shifted to the respective positions shown in FIG. 12b, whereby a parallel flow path for reintroducing the eluted sample flow into the injection valve 220 is created. During this reinjection process, there are two parallel fluid paths in both valve 215 and the injection valve 220 and the eluted sample flow is directed to the inlet of the loop valve 300 where in desired fractions are collected and stored in the sample loops 310. The valve flow paths in the injection valve 220 are schematically shown as dashed lines in FIG. 12b. As previously mentioned, the eluted fractions stored in the sample loops 310 may subsequently be further purified using column B or the like.

What is claimed is:

1. A rotary valve comprising a stator with an inner stator face, and a rotor with an inner rotor face arranged in sealing contact with the inner stator face,
wherein the rotor is rotatably movable to a plurality of rotor positions about a rotational axis relative to the inner stator face,
wherein the stator comprises a plurality of connection ports each being in fluidic contact with a corresponding valve orifice at the inner stator face and the rotor comprises two or more interconnection paths for selective fluidic interconnection of said valve orifices with respect to the rotor position,
wherein the stator comprises a first port, a second port, a third port, and a fourth port,
wherein the interconnection paths in the rotor are arranged as three generally parallel separate paths which provide selective interconnection between corresponding valve orifices, and
wherein when one of the interconnection paths is forming a fluidic interconnection and the other one or more interconnection paths are not forming fluidic interconnection, the other one or more interconnection paths do not cover valve orifices.

2. The rotary valve of claim 1, wherein the first port, the second port, the third port, and the fourth port correspond to an inlet port, an outlet port, a component feed port, and a component return port, respectively, and
wherein the rotary valve comprises a first rotor position interconnecting the inlet port with the outlet port, a second rotor position interconnecting the inlet port with the component feed port and the component return port with the outlet port, a third rotor position interconnecting the inlet port with the component return port and the component feed port with the outlet port, and a fourth rotor position interconnecting the component feed with the component return port.

3. The rotary valve of claim 1, wherein the first port, the second port, the third port, and the fourth port correspond to an inlet port, an outlet port A, an outlet port B, and an outlet port C, respectively, and
wherein the rotary valve comprises a first rotor position interconnecting the inlet port with the outlet port A and the outlet port B with the outlet port C, a second rotor position interconnecting the inlet port with the outlet port B, a third rotor position interconnecting the inlet port with the outlet port C and the outlet port A with the outlet port B.

4. A chromatography system comprising,
a first rotary valve of claim 1 as a column connection valve with the first port, the second port, the third port, and the fourth port correspond to an inlet port, an outlet port, a column feed port, and a column return port, respectively, with the column feed port fluidly connected to a first end of a chromatography column and the column return port connected to a second end of the column, and
a second rotary valve of claim 1 as an output selection valve with the second port, the third port, and the fourth port correspond to an inlet port, a fractionation port, an outlet port, and waste, respectively.

5. A fluidic circuit comprising a first and a second rotary valves of claim 2 and a first and a second fluidic components,
wherein the inlet port of the second valve is connected to the outlet port of the first valve,
the first fluidic component is connected between the component feed port of the first valve and the component feed port of the second valve, and
the second fluidic component is connected between the component return port of the first valve and the component return port of the second valve.

6. A rotary valve comprising a stator with an inner stator face, and a rotor with an inner rotor face arranged in sealing contact with the inner stator face,
wherein the rotor is rotatably movable to a plurality of rotor positions about a rotational axis relative to the inner stator face,
wherein the stator comprises a plurality of connection ports each being in fluidic contact with a corresponding valve orifice at the inner stator face and the rotor comprises two or more interconnection paths for selective fluidic interconnection of said valve orifices with respect to the rotor position,
wherein the stator comprises a first port, a second port, a third port, and a fourth port,
wherein the interconnection paths in the rotor are arranged as three generally parallel separate paths which provide selective interconnection between corresponding valve orifices, and
wherein when one of the interconnection paths is forming a fluidic interconnection and the other one or more interconnection paths are not forming fluidic interconnection, the other one or more interconnection paths do not cover valve orifices,
wherein the rotary valve comprises a first rotor position interconnecting the first port with the second port, a second rotor position interconnecting the first port with the third port and the fourth port with the third port, a third rotor position interconnecting the inlet port with the component return port and the component feed port with the outlet port, and a fourth rotor position interconnecting the third port with the fourth port.

7. The rotary valve of claim 6, wherein the first port, the second port, the third port, and the fourth port correspond to an inlet port, an outlet port, a component feed port, and a component return port, respectively, and
wherein the first rotor position interconnecting the inlet port with the outlet port, the second rotor position interconnecting the inlet port with the component feed port and the component return port with the outlet port, the third rotor position interconnecting the inlet port with the component return port and the component feed port with the outlet port, and the fourth rotor position interconnecting the component feed with the component return port.

8. The rotary valve of claim 6, wherein the first port, the second port, the third port, and the fourth port correspond to an inlet port, an outlet port A, an outlet port B, and an outlet port C, respectively, and
the first rotor position interconnecting the inlet port with the outlet port A and the outlet port B with the outlet port C, the second rotor position interconnecting the inlet port with the outlet port B, the third rotor position interconnecting the inlet port with the outlet port C and the outlet port A with the outlet port B.

9. A chromatography system comprising,
a first rotary valve of claim 6 as a column connection valve with the first port, the second port, the third port, and the fourth port correspond to an inlet port, an outlet port, a column feed port, and a column return port, respectively, with the column feed port fluidly connected to a first end of a chromatography column and the column return port connected to a second end of the column, and a second rotary valve of claim 6 as an output selection valve with the second port, the third port, and the fourth port correspond to an inlet port, a fractionation port, an outlet port, and waste, respectively, wherein the first rotary valve comprises a first rotor position interconnecting the inlet port with the outlet port, a second rotor position interconnecting the inlet port with the column feed port and the column return port with the outlet port, a third rotor position interconnecting the inlet port with the component return port and the component feed port with the outlet port, and a fourth rotor position interconnecting the component feed with the component return port, wherein the second rotary valve comprises a first rotor position interconnecting the inlet port with the fractionation port and the outlet port with the waste port, a second rotor position interconnecting the inlet port with the outlet port, and a third rotor position interconnecting the inlet port with the waste port and the fractionation port with the outlet port.

10. A fluidic circuit comprising a first and a second rotary valves of claim 7 and a first and a second fluidic components, wherein the inlet port of the second valve is connected to the outlet port of the first valve, the first fluidic component is connected between the component feed port of the first valve and the component feed port of the second valve, and the second fluidic component is connected between the component return port of the first valve and the component return port of the second valve.

11. A rotary valve comprising a stator with an inner stator face, and a rotor with an inner rotor face arranged in sealing contact with the inner stator face, wherein the rotor is rotatably movable to a plurality of rotor positions about a rotational axis relative to the inner stator face, wherein the stator comprises a plurality of connection ports each being in fluidic contact with a corresponding valve orifice at the inner stator face and the rotor comprises two or more interconnection paths for selective fluidic interconnection of said valve orifices with respect to the rotor position, wherein the stator comprises an inlet port, an outlet port A, an outlet port B, and an outlet port C, wherein the interconnection paths in the rotor are arranged as three generally parallel separate paths which provide selective interconnection between corresponding valve orifices, wherein the rotor valve comprises a first rotor position interconnecting the inlet port with the outlet port A and the outlet port B with the outlet port C, a second rotor position interconnecting the inlet port with the outlet port B, a third rotor position interconnecting the inlet port with the outlet port C and the outlet port A with the outlet port B, wherein when one of the interconnection paths is forming a fluidic interconnection and the other one or more interconnection paths are not forming fluidic interconnection, the other one or more interconnection paths do not cover valve orifices.

* * * * *